(12) United States Patent
Schrader

(10) Patent No.: US 7,872,035 B2
(45) Date of Patent: Jan. 18, 2011

(54) ANGIOTENSIN II ANTAGONISTS

(75) Inventor: Harald Schrader, Trondheim (NO)

(73) Assignee: AstraZeneca AB, Sodertalje (SE)

( * ) Notice: Subject to any disclaimer, the term of this patent is extended or adjusted under 35 U.S.C. 154(b) by 1171 days.

(21) Appl. No.: 10/311,760

(22) PCT Filed: Jun. 15, 2001

(86) PCT No.: PCT/SE01/01379

§ 371 (c)(1),
(2), (4) Date: Dec. 18, 2002

(87) PCT Pub. No.: WO01/97807

PCT Pub. Date: Dec. 27, 2001

(65) Prior Publication Data

US 2004/0092563 A1 May 13, 2004

(51) Int. Cl.
*A61K 31/41* (2006.01)
(52) U.S. Cl. .................................... 514/381
(58) Field of Classification Search ................. 514/381
See application file for complete search history.

(56) References Cited

U.S. PATENT DOCUMENTS

| 5,196,444 A | * | 3/1993 | Naka et al. .................. 514/381 |
| 5,214,153 A | | 5/1993 | Chen et al. .................. 548/252 |
| 5,703,110 A | * | 12/1997 | Naka et al. .................. 514/396 |

FOREIGN PATENT DOCUMENTS

| EP | 456510 | 11/1991 |
| EP | 510813 | 10/1992 |
| EP | 513979 | 11/1992 |
| EP | 0456136 | 3/2002 |

OTHER PUBLICATIONS

Doctor's Guide "Central Brain sites hold the key to effective migraine remedies," 1997, http://www.pslgroup.com/dg/394BA.htm.*
Hansson et al. "Headache in Mild-to-Moderate Hypertension and its Reduction by Irbesartan Therapy", Arch. Intern. Med., 2000, 160: 1654-1658.
Wolff, "Headache and Other Head Pain," New York: Oxford University Press, 1963.
Sicuteri, "Substance P and Enkephalins: A Creditable Tandem in the Pathophysiology of Cluster Headache and Migraine", Advances in Experimental Medicine & Biology, 1986, 198, Pt B:145-52.
Hannington et al., "Migraine: A Platelet Disorder", Lancet, 1981, 2; 720-3.
Lance et al., "Brainstem Influences on the Cephalic Circulation: Experimental Data From Cat and Monkey of Relevance to the Mechanism of Migraine," Headache, 1983, 23:258-65.
Welch, "Migraine. A Biobehavioral Disorder", Archives of Neurology, 1987, 44(3):323-7.

Olesen, "Clinical and Pathophysiological Observations in Migraine and Tension-Type Headache Explained by Integration of Vascular, Supraspinal and Myofascial Inputs", Pain, 1991, 46(2): 125-32.
Stewart et al., "Prevalence of Migraine Headache in the United States: Relation to Age, Income, Race, and Other Sociodemographic Factors", JAMA, 1992, 267:64-9.
Lipton et al., "Undiagnosed Migraine Headaches. A Comparison of Sympton-Based and Reported Physician Diagnosis", Archives of Internal Medicine, 1992, 152(6): 1273-8.
Celentano et al., "Medication Use and Disability Among Migraineurs: A National Probability Sample Survey", Headache, 1992, 32(5):223-8.
J. Culman et al., "The renin-angiotensin system in the brain: possible therapeutic implicatiotis for $AT_1$-receptor blockers", Journal of Human Hypertension (2002), 16, S64-S70.
Brainard, M.D., John B. "Angiotensin and Aldosterone Elevation in Salt-induced Migraine", Headaches 21:222-226,1981.
Yumiko Shibouta et al., "Pharmacological Profile of a Highly Potent and Long-Acting Angiotensin II Receptor Anatgonist . . . ", The Journal of Pharmacology and Experimental Therapeutics, 1993, vol. 266, No. 1, 114-120.
Keifu Song et al. "Inhibition of the Angiotensin II Type 1 Receptor by TCV:116: Quantitation by In Vitro Autoradiography", Japanese Journal of Pharmacology, 1999, vol. 79, No. 2, 131-139.
Y. Nishimura et al., "The angiotensin $AT_1$ receptor antagonist CV-11974 regulates cerebral blood flow and brain angiotensin $AT_1$ receptor expression", Basic Research in Cardiology, 1998, vol. 93, suppl. 2, 63-68.
William I. Bender, "ACE Inhibitors for Prophylaxis of Migraine Headaches", Headache, 1995, vol. 35, No. 8, 470-471.
"Renin-Angiotensin System: Possible Role in Headache Mechanism", Vasoactive Substance Relevant to Migraine, 1975, 90-97.

* cited by examiner

*Primary Examiner*—Shengjun Wang
(74) *Attorney, Agent, or Firm*—White & Case LLP

(57) ABSTRACT

The present invention relates to the use of an angiotensin II type 1 receptor antagonist of the general formula (I) in the manufacture of a medicament for the prophylactic and/or therapeutic treatment of a vascular headache condition such as migraine, in a subject suffering from, or susceptible to, such a vascular headache condition. A further aspect of the invention is a pharmaceutical formulation useful in any one of said vascular headache conditions, as well as a method of treatment thereof.

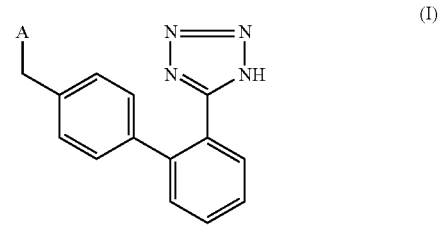

(I)

11 Claims, No Drawings

ANGIOTENSIN II ANTAGONISTS

FIELD OF THE INVENTION

The present invention relates to the use of an angiotensin II (AT II) type 1 receptor antagonist in the manufacture of a medicament for the prophylactic and/or therapeutic treatment of vascular headaches, and in particular as a medicament for the treatment of migraine. The invention further relates to a method for prophylactic and/or therapeutic treatment of a vascular headache condition encountered in a subject suffering from or susceptible to such a condition, comprising administering to the patient a therapeutically effective amount of an angiotensin II type 1 receptor antagonist.

BACKGROUND OF THE INVENTION

Migraine is a disorder that exhibits a spectrum of treatment responses in afflicted individuals. Some sufferers are fortunate and therapy may be over-the-counter remedies or even non-drug regimens using behavior modification, acupuncture, and/or hypnosis as instruments for aborting the headache. Bed rest, a darkened room, and the use of cold packs applied to the temporal artery and its branches may modify the attack. Sleep also has a beneficial effect in ending an attack. Most patients, however, will require prescription drugs for relief from the migraine. The symptoms most in need of treatment are the head pain and gastrointestinal symptoms. To a lesser degree, photophobia and the aura warrant treatment. The latter may also be quite disturbing and require treatment although its duration is relatively brief. The oral absorption of agents is less than optimal during acute migraine because of the reduced gastrointestinal peristalsis. The more severe the attack, the greater is the absorption reduced. Furthermore, the presence of nausea and frequent vomiting will preclude oral administration of pharmacological agents.

The exact pathogenesis of migraine is still unknown. Many theories have been elaborated, but none can account for all the clinical features or for all the pathophysiological aspects demonstrated in recent years. The pendulum has been swinging between vascular (Wolff 1963) and neurogenic (Sicuteri 1986) theories, with brief peripheral blood excursions (Hannington et al, 1981). In recent years, however, a general consensus has been emerging that in migraine both vascular and neural components are relevant and most probably interrelated (Lance et al, 1983; Welch 1987; Olesen 1991).

Recent epidemicologic data suggest that 17.6% of adult females and 5.7% of adult males suffer from migraine (Stewart et al, 1992). The Center for Disease Control (1991) recently reported that over the last decade the prevalence of migraine has increased by 60%. In addition, migraine is significantly under-diagnosed, with only 40% of adult females and 30% of adult males suffering from migraine being patient diagnosed (Lipton et al, 1992). Yet 80% of this population of undiagnosed patients suffering from migraine experience disability (Stewart et al, 1992), and most seek periodic medical care for other medical conditions.

Migraine is also under-treated. Only about 40% of females and 30% of males utilize prescription drugs (Celentano et al, 1992). However, many of these patients discontinue prescription medication and rely on the over-the-counter remedies.

The most common drugs, which at present are used for the treatment of migraine and other forms of vascular headaches, are e.g. triteness, ergotamine, aspirin and NSAIDS.

One major problem with the mentioned drugs is that they often have an onset time of from 60 minutes and up to 4 hours. This is a disadvantage in therapy of vascular headache conditions such a migraine.

Thus, the problem underlying the present invention is to find a new way of therapy for vascular headache conditions, and in particular migraine, with as few side effects as possible. A further problem underlying the present invention, is to find a new way of therapy providing a fast onset of action, i.e. a fast pain relief as well as relief of the symptoms associated with a vascular headache condition, to patients suffering from the vascular headache condition.

Angiotensin II (AT II) type 1 receptor antagonists are compounds which are known to interfere with the renin-angiotensin system (RAS) and are used to treat common cardiovascular diseases, particularly arterial hypertension and congestive heart failure.

Angiotensin II type 1 receptor antagonists for which the present invention has found a new medical use are thus known in the art. However, nothing has been disclosed in connection with their potential effects in prophylaxis and/or therapeutic treatment of patients suffering is from vascular headache conditions and more particularly migraine.

In *Arch. Intern. Med. Vol.* 160, June 2000, pp. 1654-1658, L. Hansson et al., discloses results from a double-blind, placebo-controlled study with irbesartan, of patients having mild-to-moderate hypertension. The use of irbesartan is, according to the authors, associated with a significant reduction in the incidence of headache commonly seen in hypertensive patients.

EP 456 510-A1 of Merck, discloses compounds which are said to exhibit AII antagonist activity by the IC50 assay.

SUMMARY OF THE INVENTION

In one embodiment, the present invention relates to a new use of an angiotensin II (AT II) type 1 receptor antagonist in the manufacture of a medicament for the prophylactic and/or therapeutic treatment of a vascular headache condition, particularly migraine, encountered in a subject suffering from, or susceptible to, such a vascular headache condition.

In a further embodiment, the present invention relates to a new method for prophylactic and/or therapeutic treatment of a vascular headache condition, in particular migraine, comprising administering to a subject suffering from, or susceptible to, such a vascular headache condition, a therapeutically effective amount of a medicament comprising an angiotensin II type 1 receptor antagonist as the active substance.

Yet another embodiment of the present invention relates to a pharmaceutical formulation for use in the prophylactic and/or therapeutic treatment of a vascular headache condition encountered in a patient suffering from, or susceptible to, such a vascular headache condition, comprising an angiotensin II type 1 receptor antagonist as the active substance in optional admixture with a pharmaceutically acceptable adjuvant, diluent or carrier.

DETAILED DESCRIPTION OF THE INVENTION

In preferred embodiments of the present invention use is made of an angiotensin II type 1 receptor antagonist of the general formula I:

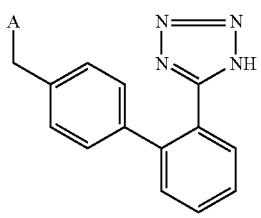

I wherein A is selected from the group consisting of any one of

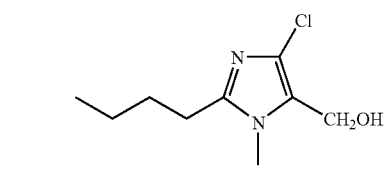

I:1

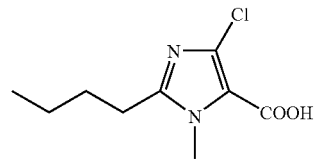

I:2

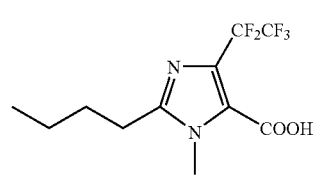

I:3

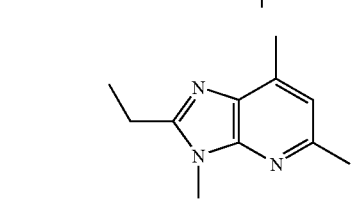

I:4

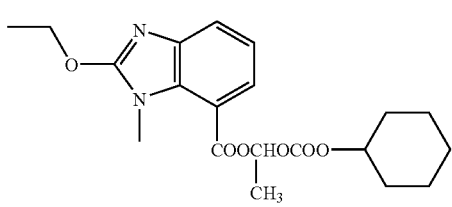

I:5

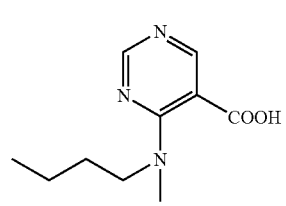

I:6

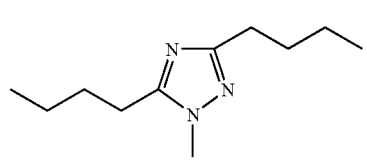

I:7

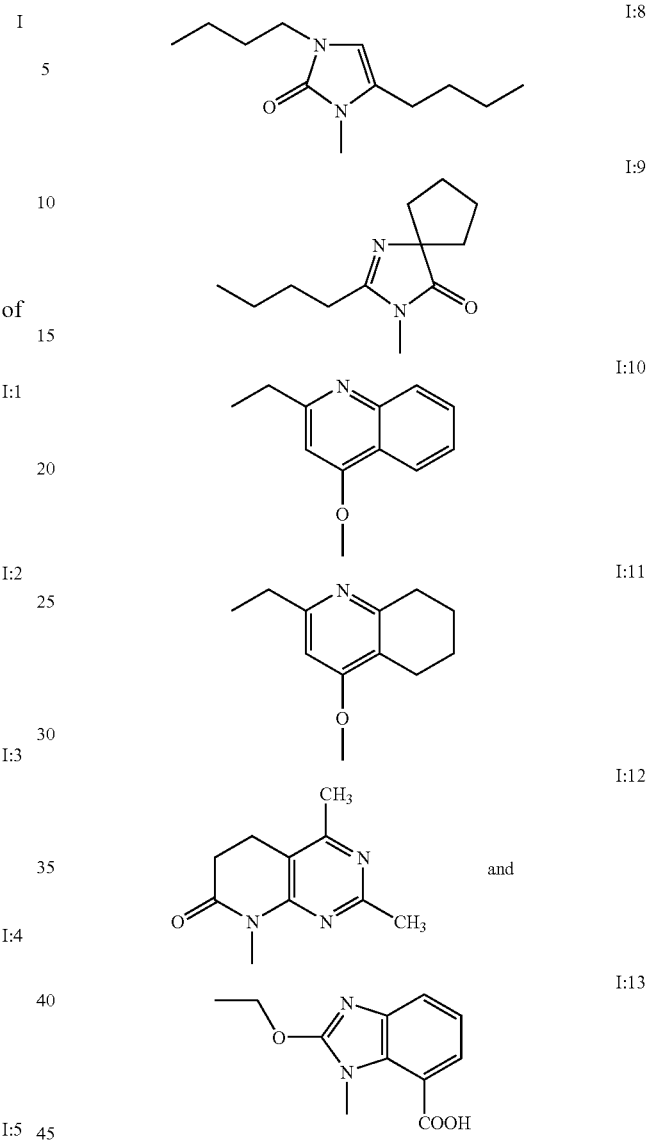

or pharmaceutically acceptable salts, solvates or stereochemical isomers of any of these, or solvates of such salts.

The compound of the general formula I wherein A is the I:1 moiety has the generic name losartan and is known from European Patent No. EP 0 253 310 B1 to du Pont.

The compound of the general formula I wherein A is the I:5 moiety has the generic name candesartan cilexetil and is known from European Patent No. 459 136 B 1 and U.S. Pat. No. 5,196,444 to Takeda Chemical Industries.

The compound of the general formula I wherein A is the I:9 moiety has the generic name irbesartan.

The compound of the general formula I wherein A is the I:13 moiety has the generic name candesartan and is known from European Patent No. 459 136 B1 and U.S. Pat. No. 5,703,110 to Takeda Chemical Industries.

In preferred embodiments of the present invention, use is made of a compound of the general formula I wherein A is I:5 (candesartan cilexetil) or A is I:13 (candesartan). Candesartan cilexetil is currently manufactured and sold worldwide e.g. under the trade names Atacand®, Amias® and Blopress®.

When the angiotensin II type 1 receptor antagonists used in the present invention have several asymmetric carbon atoms, they can consequently exist in several stereochemical forms. The present invention includes the -.nxt*re of isomers as well as the individual stereoisomers. The present invention further includes geometrical isomers, rotational isomers, enantiomers, racemates and diastereomers.

Where applicable, the angiotensin II type 1 receptor antagonists may be used in neutral form, e.g. as a carboxylic acid, or in the form of a salt, preferably a pharmaceutically acceptable salt such as the sodium, potassium, ammonium, calcium or magnesium salt of the compound at issue. Where applicable the compounds listed above can be used in hydrolyzable ester form.

In the present invention, angiotensin II type 1 receptor antagonists include all prodrugs thereof, whether active or inactive in vitro. Thus, although such protected derivatives may not possess pharmacological activity per se, they may be administered e.g. parenterally or orally, and thereafter metabolized in vivo to form pharmacologically active angiotensin II type 1 receptor antagonists.

In the present invention, the term "vascular headache condition" is intended to include any kind of vascular headaches, in particular migraine, cluster headache, post-traumatic headache, tension headache, muscular headache and headache caused by one or more vascular diseases. The present invention is preferably used for treating subjects suffering from or susceptible to, migraine. A further aspect of the invention, is a vascular headache condition not due to hypertension (i.e. not caused by hypertension).

The term "migraine" should be interpreted according to *The Headache Classification Committee of the International Headache Society, Classification and Diagnostic Criteria for Headache Disorders, Cranial Neuralgias and Facial Pain, Cephalalgia* 1988; 8 *Suppl.* 7:1-96. It is an often familial symptom complex of periodic attacks of vascular headache, usually temporal and unilateral in onset, commonly associated with irritability, nausea, vomiting, constipation or diarrhea, and often with photophobia. Attacks are preceded by constriction of the cranial arteries, usually with resultant prodromal sensory (especially ocular) symptoms, and commence with the vasodilatation that follows.

Migraine can be divided into various specific types including abdominal, acephalic, acute confusional, basilar, classic, common, complicated, fulgurating, Harris', hemiplegic, ocular, ophthalmic and ophthalmoplegic.

The term "cluster headache" is most typically defined as the temporal clustering of attacks during periods usually lasting between 2 weeks and 3 months, separated by intermissions of at least 14 days, but usually several months. This type of cluster headache is also known as "episodic cluster headache". The term "chronic cluster headache" is characterized by the absence of intermissions of at least 14 days for more than one year (*Textbook of pain*, $3^{rd}$ ed., p. 504, 1994).

The term "post-traumatic headache" is headache caused by some head trauma, whereas "tension headache" and "muscular headache" belong to the group of headaches formerly described as "muscle contraction", "psychogenic", "stress" or "essential" (*Textbook of Pain*, $3^{rd}$ ed., p. 504, 1994).

Normally, the angiotensin II type 1 receptor antagonists are administered by the oral or parenteral route, e.g. by intravenous, subcutaneous or intramuscular administration. Other possible routes of administration include rectal and transdermal administration. The formulation may be given in dosage unit form, especially as tablets or capsules.

According to a further aspect of the invention, there is provided a pharmaceutical formulation for use in the prophylactic and/or therapeutic treatment of a vascular headache condition encountered in a patient suffering from, or susceptible to, such a vascular headache condition, comprising an angiotensin II type 1 receptor antagonist as the active substance in optional admixture with a pharmaceutically acceptable adjuvant, diluent or carrier.

The wording "daily dose" is defined so that the angiotensin II type 1 receptor antagonist may be given either as a unit dosage once daily, such as a tablet or a capsule, or alternatively the angiotensin II type 1 receptor antagonist may be given twice daily. The daily dose may vary within the dosage ranges mentioned below, and depends on the patient's individual response to treatment.

With the wording "therapeutic treatment" as herein used, is meant that the vascular headache disease, such as migraine, is treated by administering an angiotensin II type 1 receptor antagonist according to the formula I above, as soon as the vascular headache, such as a migraine attack, has started to give the patient suffering therefrom, symptoms connected with the disease. This means that the use of an angiotensin II type 1 receptor antagonist according to the formula I above, provides therapy of a fully or partly developed vascular headache condition such as migraine.

With the wording "prophylactic treatment" as herein used, is meant that an angiotensin II type 1 receptor antagonist according to the formula I above, may be administered to a person to prevent the frequency of attacks with headache, to reduce the severity or the duration of the attack. Furthermore, it may be administered before the vascular headache such as the migraine attack, has started to give full symptoms or only slight symptoms.

The adjuvants, diluents and carriers used in the pharmaceutical formulations of the present invention, may be conventional ones well known to the person skilled in the art. Examples of such adjuvants, diluents and carriers include substances used as binders, lubricants, fillers, disintegrants, pH regulants and thickeners as well as substances included for providing isotonic solutions.

The dose of the angiotensin It type 1 receptor antagonist and in particular a compound according to formula I to be administered in prophylaxis and/or treatment of vascular headache conditions in subjects suffering from, or susceptible to, such conditions, will depend primarily upon the angiotensin II type 1 receptor antagonists which is used, the route of administration, the severity of the condition to be treated and the status of the subject at issue. The daily dose, especially at oral, rectal as well as parenteral administration, can be in the range of from about 0.01 mg to about 1000 mg per day of active substance, suitably from 0.1 mg to 750 mg per day of active substance, particularly from 1 mg to 500 mg per day of active substance. In preferred embodiments where candesartan and derivatives thereof are used, including candesartan cilexetil, the dosage range at oral, rectal as well as parenteral administration can be in the range of from about 0.1 mg to about 100 mg per day, particularly from 0.2 mg to 50 mg per day calculated as candesartan.

EXAMPLE

The invention is illustrated by reference to the following Example which is not intended to limit the invention in any way.

Example 1

Pilot Study Design and Case Report

A study in which the effects of the angiotensin II type 1 receptor antagonist candesartan cilexetil (Atacand®) is compared to that of placebo, was carried out to explore the feasability of giving candesartan cilexetil to patients suffering from, or susceptible to, vascular headache conditions, and especially migraine.

The pilot study was a double-blind placebo-controlled crossover trial on the prophylactic effect of the AT II antagonist candesartan cilexetil performed in patients suffering from migraine.

The study provides preliminary data on the feasibility of administering candesartan cilexetil for preventing migraine. It also provides preliminary data on useful concentrations of candesartan cilexetil in this use.

Two patients with a medical history of migraine, have provided clinical evidence for a beneficial effect of candesartan cilexetil against said disease. One patient had a significant relief of symptoms when treating himself with Atacand® (candesartan cilexetil) 16 mg. The other patient also showed a significant relief of symptoms. The relief was subjectively noted after the treatment with Atacand®.

The low number of withdrawals from the study, due to possible side-effects caused by the study medication, clearly shows that this medication is feasible and well-tolerated in patients suffering from vascular headaches such as migraine.

Example 2

Large-scale Study Design

A double-blind, placebo-controlled crossover clinical trial in which the effects of the angiotensin II type 1 receptor antagonist candesartan cilexetil (Atacand®) is compared to that of placebo, is carried out to determine the efficacy when giving candesartan cilexetil to patients for prophylactic treatment of vascular headache conditions, and especially migraine. This study follows the guidelines set forth by the "International Headache Society Committee on Clinical Trials in migraine" (Cephalalgia 1991; 11/1:1-12).

The following inclusion criteria has been applied: diagnosis of migraine with and without aura according the IHS criteria (*The Headache Classification Committee of the International Headache Society, Classification and Diagnostic Criteria for Headache Disorders, Cranial Neuralgias and Facial Pain, Cephalalgia* 1988; 8 *Suppl.* 7:1-96); male or female patient with an age between about 18 and 60 years; migraine having been present for more than one year; start of migraine before the age of 50 years and attacks of migraine occuring two to six times per month. Exclusion criteria is: interval headache that the patient would not be able to differentiate from migraine; use of migraine-prophylactic drugs in the last 4 weeks before the trial; pregnancy or inability to use contraceptives; decreased renal or hepatic function; hypersensitivity to AT II antagonists, history of angioneurotic edema or psychotic disorder.

The subjects enter a 4 weeks placebo run-in period in order to verify the attack frequency and exclude placebo responders. The non-responders would be allocated to treatment according to a computer generated randomization list by which half of the subjects would receive 12 weeks of treatment with candesartan cilexetil followed by a two week wash-out period and finally a 12 weeks lasting period with matching placebo tablets. The other half of the subjects starts with a 12 week-placebo period followed by a two week wash-out period and finally a 12 weeks lasting period during which they will be treated with candesartan cilexetil.

Throughout the study, the patients need to keep a diary recording the presence, duration and severity (1-4, mild moderate, severe or excrutating) of headache, and presence and severity of accompanying nausea, photophobia, phonophobia, use of symptomatic drugs and sick leave.

The primary efficacy parameters are
1) number of hours with headache,
2) number of days with headache, and
3) number of days during which the patient experienced migraine.

The secondary efficacy parameters are
1) headache severity index,
2) use of symptomatic drugs,
3) health-related quality of life and number of days with sick leave, and
4) acceptability of treatment.

This study aims at providing more detailed data on the feasibility of administering candesartan cilexetil to patients susceptible to migraine attacks. It also aims at providing further data on useful concentrations of candesartan cilexetil for this new use.

The invention claimed is:

1. A method for the treatment of a vascular headache condition not caused by hypertension, comprising administering to a patient in need of such treatment a therapeutically effective amount of an angiotensin II type 1 receptor antagonist selected from the group consisting of candesartan and candesartan cilexetil.

2. A method for the treatment of migraine, comprising administering to a patient in need of such treatment a therapeutically effective amount of an angiotensin II type 1 receptor antagonist selected from the group consisting of candesartan and candesartan cilexetil.

3. The method according to claim 1 or 2, wherein the treatment is therapeutic.

4. The method according to claim 1 or 2, wherein the treatment is prophylactic.

5. The method according to claim 1 or 2, wherein a daily dose of the angiotensin II type 1 receptor antagonist is in the range of from about 0.01 mg to about 1000 mg.

6. The method according to claim 5, wherein the daily dose of the angiotensin II type 1 receptor antagonist is in the range of from 0.1 mg to 750 mg.

7. The method according to claim 6, wherein the daily dose of the angiotensin II type 1 receptor antagonist is in the range of from 1 mg to 500 mg.

8. The method according to claim 7, wherein the daily dose of the angiotensin II type 1 receptor antagonist is in the range of from about 0.1 mg to about 100 mg.

9. The method according to claim 8, wherein the daily dose of the angiotensin II type 1 receptor antagonist is in the range of from 0.2 mg to 50 mg.

10. The method according to claim 1 or 2, wherein the angiotensin II type 1 receptor antagonist is administered in a dosage unit form.

11. The method according to claim 10, wherein the dosage unit form is a tablet or capsule.

* * * * *